United States Patent [19]

Kanner

[11] Patent Number: 4,653,519
[45] Date of Patent: Mar. 31, 1987

[54] RINSING APPARATUS FOR CONTACT LENS CLEANING SYSTEM

[75] Inventor: Rowland W. Kanner, Guntersville, Ala.

[73] Assignee: Ryder International Corporation, Arab, Ala.

[21] Appl. No.: 753,323

[22] Filed: Jul. 9, 1985

[51] Int. Cl.$^4$ .............................................. B08B 1/04
[52] U.S. Cl. .................................. 134/140; 134/158; 134/161; 310/104; 74/17.8; 366/273
[58] Field of Search ............... 134/137, 140, 149, 157, 134/158, 161, 112; 310/104; 366/273, 274; 74/17.8, DIG. 4; 464/29

[56] References Cited

U.S. PATENT DOCUMENTS

| | | | |
|---|---|---|---|
| 2,466,468 | 4/1949 | Neal | 366/274 |
| 3,006,557 | 10/1961 | Jacobs | 134/181 X |
| 3,614,959 | 10/1971 | Schollmaier et al. | 366/274 X |
| 3,623,492 | 11/1971 | Frantz et al. | 134/149 X |
| 3,770,113 | 11/1973 | Thomas | 134/143 X |
| 3,815,115 | 6/1974 | Inque | 366/273 X |
| 3,871,395 | 3/1975 | Murry | 134/143 X |
| 4,090,263 | 5/1978 | Hoffa | 366/273 |
| 4,127,137 | 11/1978 | Butcher | 366/273 X |
| 4,199,265 | 4/1980 | Sanderson et al. | 366/274 |
| 4,465,377 | 8/1984 | de Bruyne | 366/273 |

FOREIGN PATENT DOCUMENTS

| | | | |
|---|---|---|---|
| 2142438 | 11/1978 | Fed. Rep. of Germany | 366/273 |
| 55-107158 | 8/1980 | Japan | 74/DIG. 4 |

Primary Examiner—Philip R. Coe
Assistant Examiner—Frankie L. Stinson
Attorney, Agent, or Firm—Trexler, Bushnell & Wolters, Ltd.

[57] ABSTRACT

A rinsing apparatus is provided for a contact lens cleaning system. This rinsing apparatus comprises a container for receiving a quantity of rinsing fluid, receptacles for receiving contact lenses and an agitator mounted in the container for a compound agitating motion and coupled to the receptacles for agitating the receptacles. A base unit includes a platform for mounting the container in a stationary position and a drive assembly for driving the agitator to achieve the desired compound agitating motion. Advantageously, this drive assembly is operatively coupled with the agitator only by a magnetic coupling arrangement, obviating the need for any mechanical connection or coupling therebetween, or for extending any rotating members through the container.

19 Claims, 13 Drawing Figures

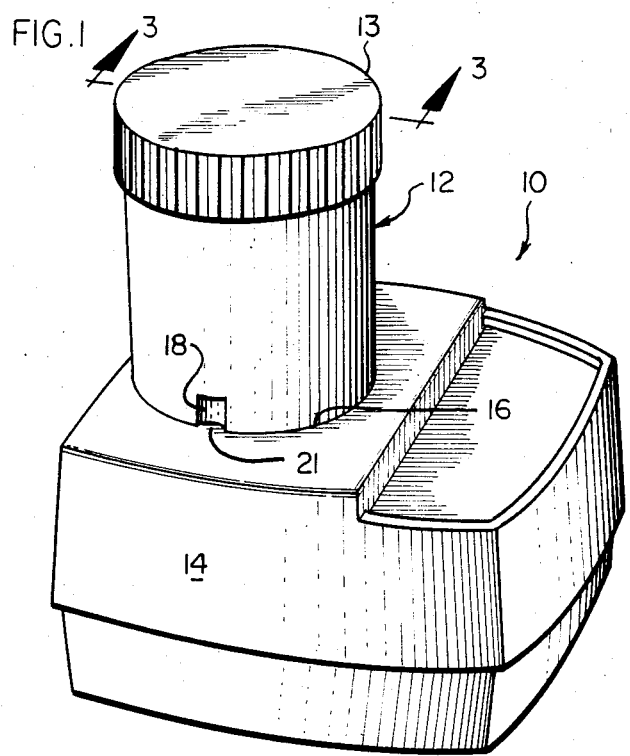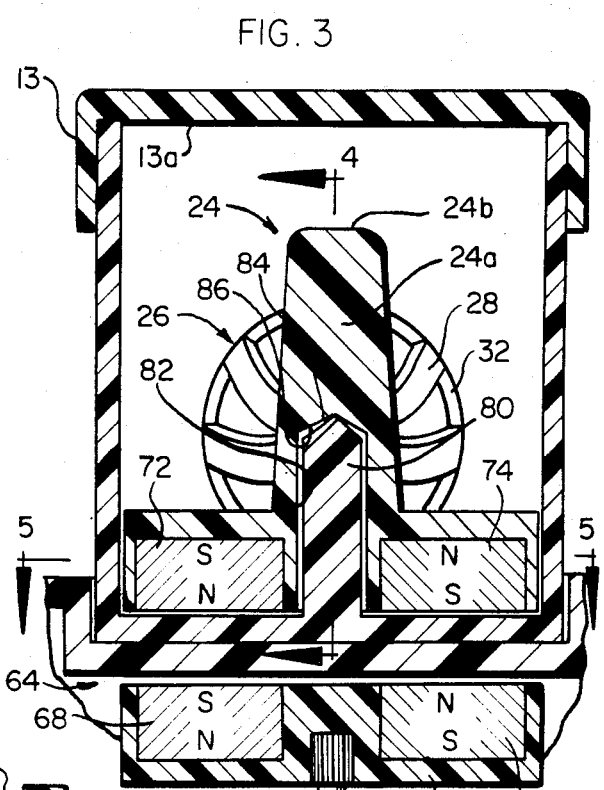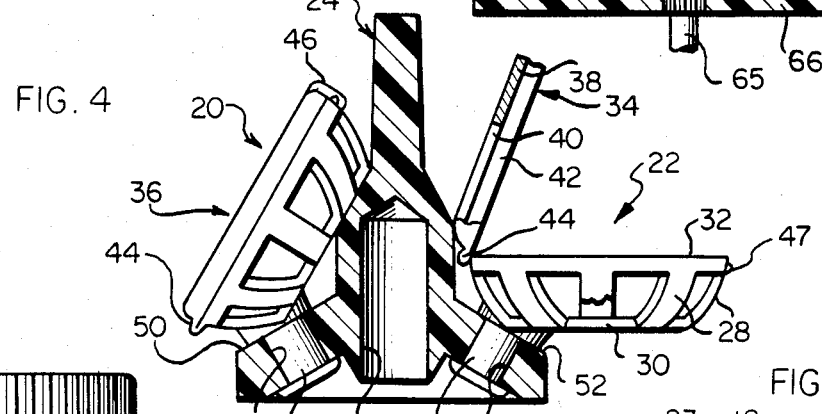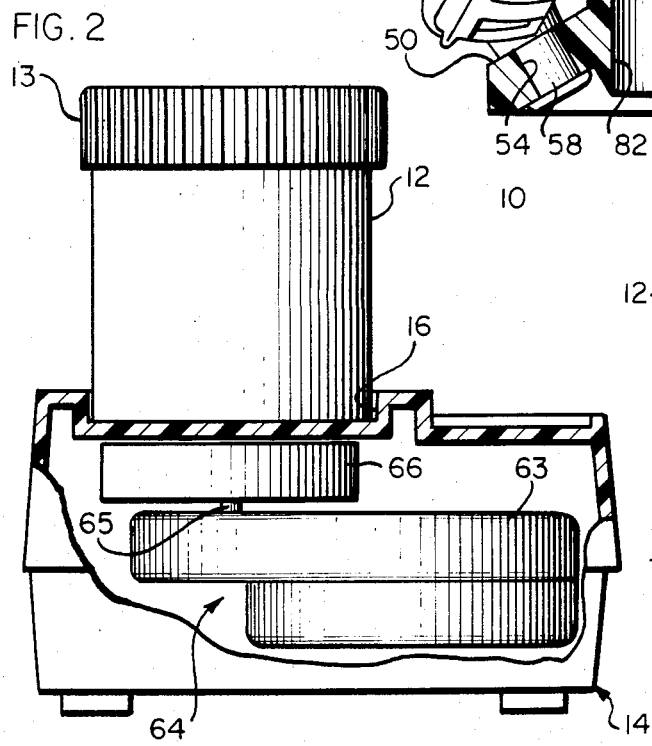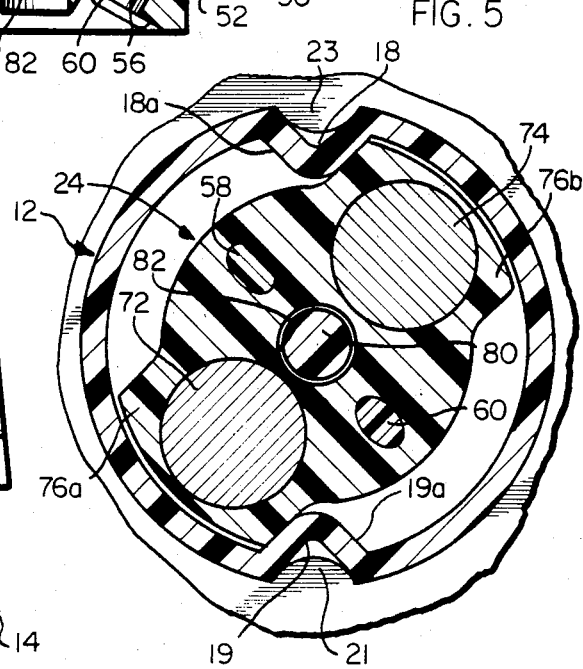

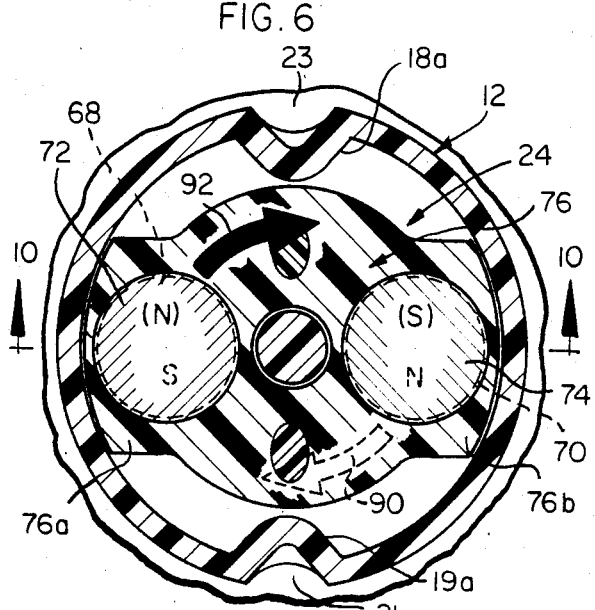
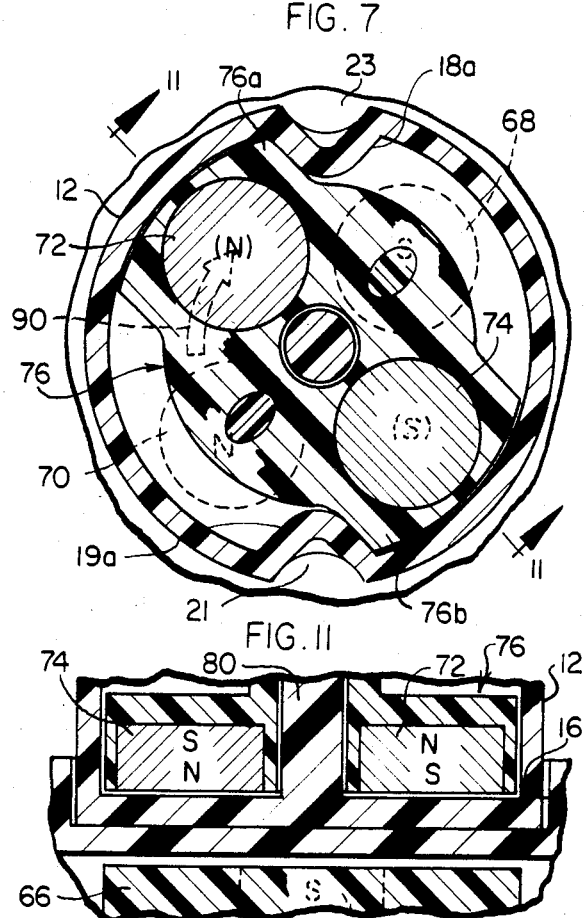
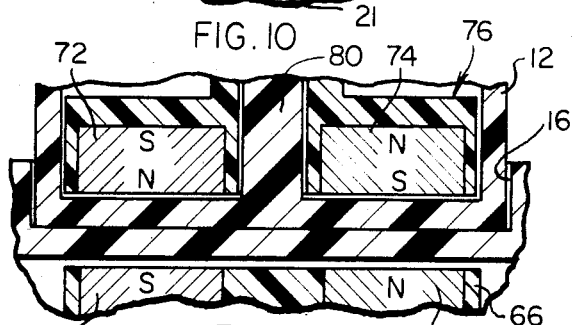
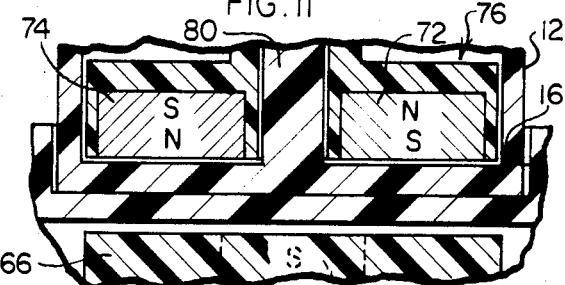
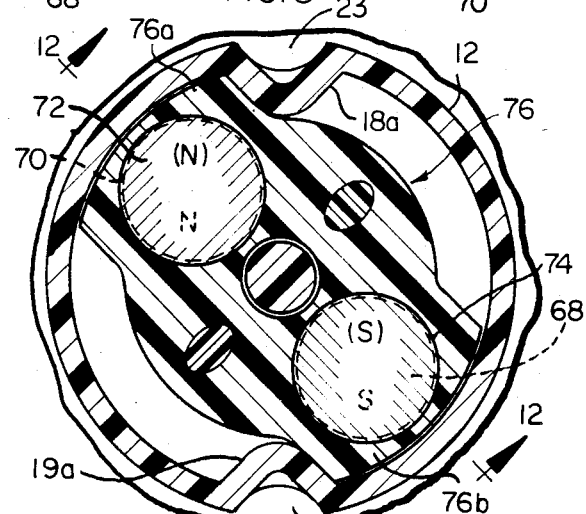
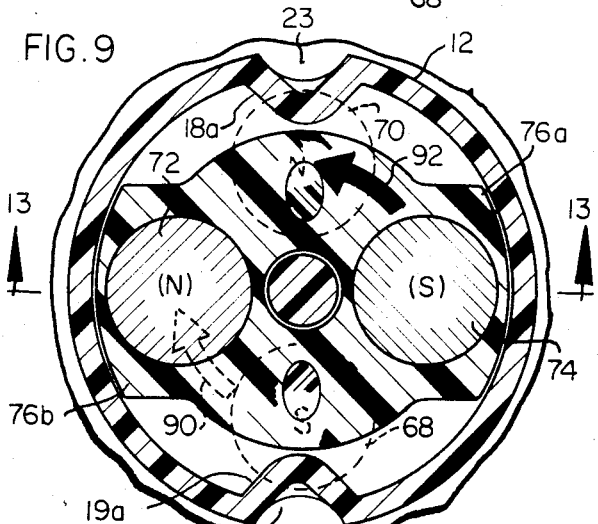
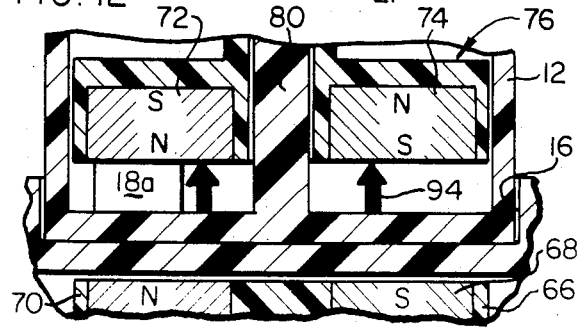
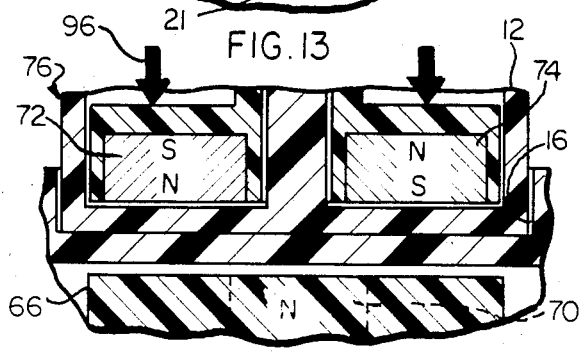

RINSING APPARATUS FOR CONTACT LENS CLEANING SYSTEM

BACKGROUND OF THE INVENTION

This invention is directed generally to the field of cleaning apparatus or systems for contact lenses and more particularly to a novel and improved apparatus for effecting a post-cleaning rinsing of contact lenses by agitating the contact lenses in a rinsing solution.

Development of improved methods and apparatus for cleaning of contact lenses has assumed new importance with the advent of soft contact lenses and extended wear contact lenses. Both of these newer types of lenses are relatively porous as compared to the older "hard" lenses. Because these lenses are additionally intended for relatively longer periods of wear, thorough cleaning is necessary to remove residue which may have accumulated during wearing. In this regard, the relative porosity of these types of contact lenses tends to encourage collection and retention of proteinaceous and fatty body fluids. This results in a buildup of residues not only on the surfaces of the lenses but also within the pores thereof.

Moreover, such soft and extended wear contact lenses are generally hydrophilic, as well as porous, such that the proteinaceous and fatty materials or other contaminants tend to invade the porous matrix of the lenses. Frequently, an enzymatic cleaning solution of a generally available type is utilized for cleaning such lenses. The enzymes in such cleaning solutions tend to destroy or consume the proteinaceous and fatty substances which are present on the lenses. However, after subjecting the lenses to such an enzyme cleaning solution, they must be rinsed before placement on the eye. That is, since the enzyme solutions are hostile to body tissues, they would have an adverse effect if permitted to remain upon or within the porous lens after it is replaced on the eye.

Moreover, it should be recognized that enzyme cleaning procedures generally involve leaving the contact lenses in the enzyme solution for a period of six to twelve hours. Hence, there is often considerable penetration of the porous matrix of the lenses by the enzyme solution. Accordingly, it is important that the contact lenses be thoroughly rinsed to assure removal of any residual cleaning solution therefrom following the cleaning procedure. As mentioned above, such rinsing is necessary to assure that those materials which attack protein or potein-like substances will not remain on the lenses, and more particularly, within the pores thereof, when they are replaced on the eye.

The prior art has proposed utilizing a rotary unit to spin the lens in a rinsing solution-filled case, to effect such rinsing following enzyme cleaning. One such apparatus is shown in U.S. Pat. No. 3,623,492. However, the constant rotation of this type of device tends to cause more agitation of the rinsing solution at the periphery of the case than at the central portion thereof where the lens or lenses are disposed. This may result in insufficient agitation of the rinsing solution about the lenses themselves, as is necessary to effect thorough rinsing.

Accordingly, a problem has arisen in designing a container which will not only contain the lens or lenses but also provide sufficient open volume for proper agitation of the rinsing solution or water about lens or lenses. However, the solid lenses, when placed in this liquid solution or water tend to migrate to the areas of least agitation or net liquid flow within the container or case. Moreover, relatively thin, "soft" type lenses have a tendency to in effect "roll up" and migrate toward or even past through openings provided for liquid flow, to reach areas of minimum or no flow. It will be appreciated that such migration of the lenses defeats the purpose of agitation, resulting in possibly insufficient rinsing and penetration of the porous lens body to effect complete removal of the enzyme solution and their residues.

Moreover, the rotary device as proposed by the above prior art patent requires some form of seal where a rotary shaft or other rotation-imparting member passes through or into the solution-filled container. It will be appreciated that providing a reliable seal between relatively rotating parts always presents problems in design and fabrication. It is also known that rotating parts tend to experience wear while in service, necessitating periodic repair or replacement, or possibly leading to unsatisfactory operation or even failure. Additionally, the device shown in the above-referenced U.S. Pat. No. 3,623,492 is a manually operated device. Accordingly, there is some problem of possible user fatigue or simply of failure of the user to operate the device for a sufficient length of time or with sufficiently vigorous action to obtain the desired rinsing action.

OBJECTS AND SUMMARY OF THE INVENTION

Accordingly, it is a general object of the invention to provide a novel and improved rinsing apparatus for a contact lens cleaning system for rinsing cleaning fluids from porous contact lenses.

A more specific object is to provide an improved apparatus in accordance with the foregoing object wherein agitation of the rinsing solution or fluid with respect to the lenses is obtained during the rinsing operation, while avoiding the above-discussed problems.

A related object is to provide a rinsing apparatus for a contact lens cleaning system in accordance with the foregoing objects which is relatively simple and inexpensive in its design and construction and yet highly reliable in operation.

Briefly, and in accordance with the foregoing objects, a contact lens rinsing apparatus in accordance with the invention comprises a container; receptacle means in said container for receiving contact lenses therein; agitator means mounted in said container for compound agitating motion for agitating said receptacle means; a base member including platform means for receiving said container thereupon and drive means for driving said agitator means in said compound agitating motion; and magnetic coupling means for operatively coupling said agitator means with said drive means.

BRIEF DESCRIPTION OF THE DRAWINGS

The features of the present invention which are believed to be novel are set forth with particularity in the appended claims. The organization and manner of operation of the invention, together with further objects and advantages thereof, may best be understood by reference to the following description taken in connection with the accompanying drawings, in which like reference numerals identify like elements, and in which:

FIG. 1 is a perspective view of an assembled rinsing apparatus in accordance with the invention;

FIG. 2 is a side elevation, partially broken away and partially in section, illustrating further features of portions of the apparatus of the invention;

FIG. 3 is an enlarged partial sectional view taken generally in the plane of the line 3—3 of FIG. 1 and illustrating a portion of the apparatus thereof;

FIG. 4 is a partial sectional view taken generally in the plane of the line 4—4 of FIG. 3 showing further features of portions of the apparatus of the invention;

FIG. 5 is a sectional view taken in the plane of the line 5—5 in FIG. 3;

FIGS. 6, 7, 8 and 9 are sectional views, similar to FIG. 5, illustrating the sequence of operation of the apparatus of the invention; and FIGS. 10, 11, 12 and 13 are partial sectional views similar to FIG. 3 and taken in the planes of respective lines 10—10, 11—11, 12—12 and 13—13 of FIGS. 6, 7, 8 and 9, respectively.

DETAILED DESCRIPTION OF THE ILLUSTRATED EMBODIMENT

Referring now to the drawings and initially to FIGS. 1 through 5, a rinsing apparatus in accordance with the invention is designated generally by the reference numeral 10. Generally speaking, the rinsing apparatus 10 includes a container 12 for receiving a quantity of rinsing fluid therein and a base member or unit 14 which provides a flat, stable base or platform 16 for receiving the container 12 in a stationary position thereupon.

In the illustrated embodiment, the container 12 has a removable top closure or lid 13. Preferably, the platform 16 comprises a recessed platform, as best viewed in FIG. 2, in a top surface of the base member or unit 14. Moreover, the container 12 and recessed platform 16 include cooperating positioning means for mounting the container in a stationary and non-rotatable position relative to the platform 16 and base unit 14. These cooperating positioning means include a pair of oppositely disposed recesses 18, 19 in the container 20, a pair of oppositely disposed complementary projections 21, 23 in the recessed platform 16 for engaging these recesses 18 and 19.

Receptacle means comprising a pair of similar receptacles 20, 22 are mounted to an agitator member or agitator means 24. The agitator 24 is mounted in the container 12 for a compound agitating motion which will be described presently. Hence, this compound agitating motion is imparted to the receptacles 20, 22 and contact lenses therein.

Moreover, it will be seen that the receptacles 20 and 22 have a plurality of through openings 26 therein, defining generally a basket-like configuration, for facilitating the circulation of rinsing fluid therethrough and thereby imparting the agitation of the fluid caused by the agitator 24 to the lenses (not shown) therein. As best viewed in FIGS. 3 and 4, each of receptacles 20 and 22 comprises a basket-like member comprising a generally circular base or bottom portion 30 from which extend a plurality of ribs 28 joining with a generally annular upper rim portion 32. The ribs 28, base 30 and annular rim 32 define therebetween the openings 26 for circulation of fluid.

The receptacles are also provided with releasably locking closure means comprising lids 34, 36 which are respectively hingedly joined to the basket-like members. These lids 34, 36 are configured similarly to the basket members, comprising a central base or web portion 38 having a plurality of spokes or strips of material 40 projecting radially outwardly therefrom to an outer annular rim 42, and thus defining a further plurality of the openings 26 therein for circulation of fluid therethrough. The hinged joining of these lids to the respective basket-like members is provided by an integrally molded resilient hinge member or portion 44. Additionally, projecting snap-lock means in the form of a downwardly projecting locking member 46 at an edge of each lid generally opposite the hinge member 44 are provided for resiliently, releasably engaging facing locking tabs or projections 47 on the rim 32 of each receptacle.

As best viewed in FIGS. 3 and 4, the agitator 24 is removably mounted within container 12. The receptacles 20, 22 are mounted to the agitator 24 for movement between a generally vertical position (as indicated for receptacle 20) for agitation thereof in unison with the motion of the agitator 24, and a generally horizontal position (as indicated for receptacle 22) for facilitating the deposit and removal of contact lenses. In this regard, the agitator and receptacles include cooperating mounting means for mounting the receptacles for generally pivotal motion between the two positions illustrated in FIG. 4.

These mounting means comprise a pair of generally outwardly and downwardly sloped surfaces 50, 52 on the body of the agitator 24, each having a bearing aperture 54, 56 therethrough. Additional pin or shaft means or members 58, 60 are provided on a side surface of each of the receptacles 20, 22 for pivotal or rotatable engagement with the bearing aperture 54, 56. It will be seen that the pins or shafts are disposed at a complementary angle with respect to the slope of surfaces 50, 52 to obtain rotation or pivotal movement of the basket-like receptacles between the generally vertical and generally horizontal positions illustrated in FIG. 4.

Referring now to FIG. 2, in accordance with another feature of the invention, drive means designated generally by reference numeral 62 are provided for driving the agitator means in the compound agitating motion to be described below, for agitating the receptacles and contact lenses therein relative to the fluid in container 12. In accordance with an important feature of the invention, the drive means are not mechanically coupled with the agitator 24. Rather, novel magnetic coupling means designated generally by reference numeral 64 are provided for operatively coupling the agitator means 24 with the drive means 62. In this regard, the drive means 62 includes a rotatable member or means 66 which is rotatable relative to the stationary container 12. The drive means 62 also includes motor means, preferably comprising a small electrical motor 63 which is selectively energizable for rotating the rotatable member 66, by means of a drive shaft 65 coupled therebetween.

The magnetic coupling means will be seen to comprise drive magnet means comprising a pair of magnets 68, 70 coupled with the drive means 62 and agitator magnet means comprising a second pair of similar magnets 72, 74 coupled with the agitator 24 and positionable with respect to the drive magnets to be driven thereby. In this regard, both the drive means and agitator means include carrier portions alignable in parallel spaced apart condition for receiving the magnets 68, 70 and 72, 74. The previously mentioned rotatable means or member 66 of drive means 64 comprises the carrier for magnets 68 and 70, while a base portion 76 of the agitator 24 comprises the carrier for receiving magnets 72 and 74. The magnets mounted to each of these carriers will be seen to be generally spaced apart and centered about a common center line thereof. Moreover, the poles of each one of each of the pairs of magnets will be seen to be in reverse orientation with respect to the poles of the other one of the pair. That is, the poles of magnet 72 are in reverse orientation with respect to the poles of magnet 74, and the poles of magnet 68 are in reverse orientation with respect to the poles of magnet 70.

Advantageously, the inwardly directed positioning recesses 18 and 19 of container 12 also define inwardly projecting rotational stops 18a, 19a interiorly of container 12. These surfaces 18a, 19a cooperate with the agitator for limiting the rotation of the agitator 24 to substantially less than 180 degrees of rotation in either direction. In this regard, the base portion 76 of agitator 24 is generally circular in configuration, having a pair of similar oppositely outwardly projecting portions 76a and 76b. These portions 76a and 76b accommodate the magnets 72 and 74, and more importantly, provide cooperating stop or abutment surfaces for abutment with the stop surfaces 18a and 19a of the container 12, to so limit rotation of the agitator with respect thereto. As will presently be seen, these rotational limits help to achieve the compound agitating motion of the agitator 24 in response to constant, unidirectional rotation of motor 63 and carrier or rotatable member 66.

In this latter regard, the agitator 24 is mounted to permit both bidirectional rotation and vertical motion relative to container 12. Mounting means for this purpose comprise a centrally located upwardly projecting shaft member 80, preferably integrally projecting from a bottom wall of the container 12, and a cooperating bearing aperture 82 in agitator 24 for receiving the shaft 80. As will be presently seen, this mounting means further includes means for limiting the relative vertical motion between the agitator and the container to an amount less than the height of the rotational stops 18a and 19a. This assures that the rotational stops will in all cases stop rotation of the agitator 24 in either direction, and that the agitator will not be moved past or "jump" over these stops during rotation.

Referring now also to FIGS. 6 through 13, the compound agitating motion achieved by the structure thus far described will be briefly discussed. For purposes of discussion, the starting point of the agitator 24 and carrier member 66 will be assumed to be that illustrated generally in FIG. 5, that is, with the agitator 24 engaged against both of stops 18a and 19a, but free to move in a clockwise direction as viewed in FIG. 5. It will also be assumed that the respective poles of the magnets of the agitator 24 and of carrier 66 are aligned with opposite poles facing. That is, as illustrated in FIG. 3 for example, south pole of magnet 68 faces north pole of magnet 72 and north pole of magnet 70 faces south pole of magnet 74. Accordingly, and as illustrated in FIGS. 6 and 10, initial rotation of the carrier or rotatable member 66 in the clockwise direction, as indicated by phantom arrow 90, will result in corresponding rotation of the agitator 24 in the clockwise direction as indicated by arrow 92, due to the mutual attraction of the aligned opposite magnetic poles.

Rotation in the clockwise direction will be seen to continue until the agitator 24 reaches the position illustrated in FIGS. 7 and 11, that is, abutting the rotational stops 18a and 19a of the container 12. Thereupon, the rotatable member or carrier 66 continues to rotate, as driven by motor 63, so that the respective magnets 68 and 70 thereof rotate out of alignment with magnets 72 and 74.

Upon continued rotation of carrier 66, the magnets 68 and 70 will again come into alignment with magnet 72 and 74 as illustrated in FIGS. 8 and 12. However, it will be noted that like poles of the respective magnets are now in alignment with each other. Accordingly, the agitator 24 will be driven upwardly as indicated by arrows 94 in FIG. 12, due to the repulsion of these aligned like magnetic poles. This vertical or upward movement of agitator 24 comprises a further portion of the compound agitating motion thereof. In this regard, it will be remembered that the vertical movement is limited to an extent less than the height of the respective stops 18a and 19a. Hence, vertical movement of agitator 24 to an extent less than the height of stop 18a is illustrated in FIG. 12.

Finally, and referring to FIGS. 9 and 13, as the carrier 66 continues to rotate, magnets 68 and 70 will again approach a position wherein respective poles thereof will be aligned with the opposite poles of magnets 72 and 74, thus attracting magnets 72 and 74 and causing rotation thereof in a counterclockwise direction, as indicated by arrow 92, to again engage stops 18a and 19a. The agitator 24 will of course have moved back vertically downwardly upon shaft 80, since the repulsive magnetic forces holding it in the elevated position indicated in FIG. 12 are no longer present, due to the continued movement of magnets 68 and 70. This vertical downward or return motion is indicated generally by arrow 96 in FIG. 13. It will be seen that with continued rotation in the direction indicated by arrow 92 in FIG. 9, the agitator 24 will return to the initial position thereof illustrated in FIG. 5, engaged with stops 18a, 19a. Hence, the cycle of motion illustrated in FIGS. 6 through 9 and Figs. 10 through 13 is repeated with continued rotation of the carrier 66 and magnets 68 and 70 thereon.

Referring now again to FIGS. 1 through 5, further details of the structure of the apparatus of the invention will now be described. As previously indicated, the container 12 comprises a generally hollow and preferably cylindrical member. The mounting shaft 80 for mounting the agitator 24 is substantially axially centered in the container, extendingly upwardly from a bottom wall thereof. The inwardly projecting rotational stops or abutment means 18a, 19a on the container engage or abut the cooperating rotational stops or abutment surfaces defined by either side surface of the projecting portions 76a, 76b of the base or carrier portion of the agitator 24.

It will be noted that the means for mounting the agitator to the container further includes a vertical body portion 24a of the agitator 24 which generally extends upwardly from the carrier portion 76 thereof. Interiorly of carrier portion 76 and this vertical body portion 24a, the bearing aperture 82 extends generally vertically for receiving the shaft 80 therein. Both the shaft 80 and the bearing aperture 82 have complementary bearing surfaces 84 and 86. These bearing surfaces define a needle bearing for facilitating substantially friction-free relative rotation between the shaft 80 and the agitator 24. Moreover, the bearing aperture is of somewhat lesser axial extent or length than the shaft so as to hold the agitator 24 out of engagement with the bottom inner surface of the container, to further minimize friction during rotation of the agitator.

Accordingly, the extent of relative vertical motion between the agitator means and the container is defined by the height of the inner top surface 13a of the lid 13 of the container relative to the height of the agitator 24 as supported upon the shaft 80. That is, the distance between the top most surface 24b of the agitator 24 and undersurface 13a of closure 13 as viewed in FIG. 3 is less than the height of the rotational stop members 18a and 19a (see FIG. 12). Hence, the effective height of these stops 18a, 19a is of greater vertical extent than the extent of vertical motion permitted between the agitator and the container.

While particular embodiments of the invention have been shown and described in detail, it will be obvious to those skilled in the art that changes and modifications of the present invention, in its various aspects, may be made without departing from the invention in its broader aspects, some of which changes and modifications being matters of routine engineering or design, and others being apparent only after study. As such, the scope of the invention should not be limited by the particular embodiment and specific construction described herein but should be defined by the appended claims and equivalents thereof. Accordingly, the aim in the appended claims is to cover all such changes and modifications as fall within the true spirit and scope of the invention.

The invention is claimed as follows:

1. A rinsing apparatus for a contact lens cleaning system comprising: a container for receiving a quantity of rinsing fluid; receptable means for receiving contact lenses therein; agitator means mounted in said container for compound agitating motion and coupled with said receptacle means for agitating said receptacle means; a base member including platform means for receiving said container in a stationary position thereupon and drive means for driving said agitator means in said compound agitating motion; magnetic coupling means for operatively coupling said agitator means with said drive means; mounting means for mounting said agitator means for rotation relative to said container; and rotational stop means for limiting rotation of said agitator means to thereby achieve said compound agitating motion in response to rotation of said drive means; said compound agitating motion comprising rotation of both said agitator means and said drive means in a first direction in response to attraction of opposite poles of the respective magnets of the drive means and agitator means until said rotational stop means limits rotation of said agitator means in said first direction, followed by vertical motion of said agitator means away from said base member in response to alignment of like magnetic poles of the magnets of the drive means and agitator means as said drive means continues rotation, followed by rotation of said agitator means in a direction opposite the rotation of said drive means until stopped by said rotational stop means in response to attraction of opposite poles of the magnets of said drive means approaching the poles of the magnets of said agitator means.

2. Apparatus according to claim 1 wherein said magnetic coupling means comprises drive magnet means coupled with said drive means and agitator magnet means coupled with said agitator means and positionable with respect to said drive magnet means to be driven thereby.

3. Apparatus according to claim 1 wherein said drive means and said agitator means include carrier members alignable in parallel and spaced apart condition; and a pair of magnets mounted to each of said carrier members spaced apart along and centered about a common center line thereof; the poles of each one of each said pair of magnets being in reverse orientation with respect to the poles of the other one of each of said pair of magnets.

4. Apparatus according to claim 3 wherein said drive means further includes motor means selectively energizeable for rotating the carrier member thereof.

5. Apparatus according to claim 1 wherein said mounting means further mount said agitator means for vertical motion relative to said container, and further including means for limiting relative vertical motion therebetween to an amount less than the effective height of said rotational stop means.

6. Apparatus according to claim 1 wherein said agitator means includes mounting means for mounting said receptacle means thereto for pivotal motion between a generally vertical position for agitation thereof in unison with the motion of said agitator means and a generally horizontal position for facilitating the deposit and removal of contact lenses.

7. Apparatus according to claim 6 wherein said receptacle means comprises a pair of basket-like members, each having releasably locking closure means and a plurality of through apertures to permit circulation of said rinsing fluid therethrough.

8. Apparatus according to claim 7 wherein said mounting means comprises a pair of oppositely outwardly sloped surfaces on said agitator means each having a bearing aperture extending inwardly thereof, and pin means on each of said basket-like receptacles engaged with said bearing apertures and disposed at a complementary angle with respect to said sloped surfaces for pivoting of said basket-like members about said pin means between said substantially vertical and said substantially horizontal positions.

9. Apparatus according to claim 8 wherein said agitator means is removably rotatably mounted in said container to permit removal thereof for pivoting of said receptacles to said horizontal position for deposit and removal of contact lenses.

10. Apparatus according to claim 7 wherein said releaseably locking closure means comprises lid means respectively hingedly joined to said basket-like members and cooperating releasable snap-locking means on said lid means and said basket-like members for releasably engaging said lid means in a closed position relative to said basket-like members.

11. Apparatus according to claim 1 wherein said container comprises a generally hollow member, wherein said mounting means comprises shaft means centered in said container for rotatably receiving said agitator means thereon, and wherein said rotational stop means comprises inwardly projecting abutment means on said container and outwardly projecting abutment means on said agitator means for engagement therewith.

12. Apparatus according to claim 11 and further including means for mounting said receptacle means to said agitator means for movement in unison therewith.

13. Apparatus according to claim 11, said mounting means further including a vertical body portion of said agitator means and an elongate bearing aperture through a bottom surface of said agitator means and within said vertical body portion for receiving said shaft means therein; said shaft means and said bearing aperture having complementary bearing surfaces for facilitating substantially friction-free relative rotation between the shaft means and agitator means; and said bearing aperture being of lesser axial extent than said shaft so as to hold said agitator means out of engagement with a bottom surface of said container to further minimize friction during rotation of the agitator means.

14. Apparatus according to claim 13 wherein the extent of vertical motion between said agitator means and said container is defined by the height of an inner top surface of said container relative to the height of an outer top surface of said agitator means as supported upon said shaft means.

15. Apparatus according to claim 14 wherein said rotational stop means are of greater effective vertical extent than the extent of vertical motion permitted between said agitator means and said container.

16. Apparatus according to claim 14 wherein said container has a removable top closure member defining said inner top surface and to permit removal of said agitator means therefrom for deposit and removal of contact lenses with respect to said receptacle means.

17. A rinsing apparatus comprising: a container for receiving a quantity of rinsing fluid; agitator means carried by said container and capable of movement relative to said container, and said agitator means including receptacle means for receiving contact lenses therein; said receptacle means having a plurality of through openings therein for circulation of said rinsing fluid therethrough; drive means including means rotatable relative to said container; magnetic coupling means for operatively coupling said rotatable means for driving said agitator means in such a way as to produce arcuate as well as vertical movement of said agitator means thereby to achieve a compound agitating motion thereof; mounting means for mounting said agitator means for rotation relative to said container and rotational stop means for limiting rotation of said agitator means to thereby achieve said compound agitating motion in response to rotation of said drive means; said compound agitating motion comprising rotation of both said agitator means and said drive means in a first direction in response to attraction of opposite poles of the respective magnets of the drive means and agitator means until said rotational stop means limits rotation of said agitator means in said first direction, followed by vertical motion of said agitator means away from said base member in response to alignment of like magnetic poles of the magnets of the drive means and agitator means as said drive means continues rotation, followed by rotation of said agitator means in a direction opposite the rotation of said drive means until stopped by said rotational stop means in response to attraction of opposite poles of the magnets of said drive means approaching the poles of the magnets of said agitator means.

18. A rinsing apparatus according to claim 17 and further including mounting means for mounting said agitator means for rotation relative to said container and rotational stop means having a predetermined effective height for limiting rotation of said agitator means to less than 180 degrees of rotation in either direction, to thereby achieve said compound agitating motion in response to rotation of said drive means.

19. Apparatus according to claim 18 wherein said mounting means further mount said agitator means for vertical motion relative to said container and further including means for limiting relative vertical motion therebetween to an amount less than the effective height of said rotational stop means.

* * * * *